United States Patent
Mbagwu et al.

(10) Patent No.: US 12,029,686 B2
(45) Date of Patent: Jul. 9, 2024

(54) DESCEMETORHEXIS CREATION DEVICE

(71) Applicants: The Board of Trustees of the Leland Stanford Junior University, Stanford, CA (US); The United States of America as represented by The Department Of Veterans Affairs, Washington, DC (US)

(72) Inventors: Michael Mbagwu, Mountain View, CA (US); David Buickians, Glendale, CA (US); David Myung, Saratoga, CA (US)

(73) Assignees: The Board of Trustees of the Leland Stanford Junior University, Stanford, CA (US); The United States Government as represented by the Department of Veterans Affairs, Washington, DC (US)

( * ) Notice: Subject to any disclaimer, the term of this patent is extended or adjusted under 35 U.S.C. 154(b) by 284 days.

(21) Appl. No.: 17/695,484

(22) Filed: Mar. 15, 2022

(65) Prior Publication Data
US 2022/0287883 A1    Sep. 15, 2022

Related U.S. Application Data

(60) Provisional application No. 63/161,293, filed on Mar. 15, 2021, provisional application No. 63/161,316, filed on Mar. 15, 2021.

(51) Int. Cl.
*A61F 9/013*    (2006.01)
(52) U.S. Cl.
CPC ................................ *A61F 9/0133* (2013.01)

(58) Field of Classification Search
CPC .. A61F 9/007; A61F 9/00709; A61F 9/00736; A61F 9/00754; A61F 9/00763;
(Continued)

(56) References Cited

U.S. PATENT DOCUMENTS

| 2010/0241130 A1* | 9/2010 | Deli | A61F 9/00754 606/166 |
| 2018/0078414 A1* | 3/2018 | Deli | A61F 9/0133 |
| 2018/0271704 A1* | 9/2018 | Lifshitz | A61F 9/00754 |

FOREIGN PATENT DOCUMENTS

| EP | 2491890 A1 | 8/2012 | |
| KR | 20110072158 | * 6/2011 | A61F 9/01 |

(Continued)

OTHER PUBLICATIONS

KR20110072158 (English translation via Espacenet) (Year: 2011).*

*Primary Examiner* — Robert A Lynch

(57) ABSTRACT

Precise concentric, symmetric, and repeatable circular scoring (cutting) of Descemet's membrane is made possible by a handheld surgical ophthalmic device. The precision of the cut is provided by a stabilizing point on a stabilizing arm as well the anchoring insertion point at the limbus. Stabilization through the insertion point and the stabilizing arm provides a two-point fixation thereby establishing a cutting plane. The cutting plane allows for precise depth of cut whereas the rotating blade's consistent radius allows for circularity of the cut. The stabilization arm fixates on tissue, and is then removed when the procedure is completed. Consistent torque and contact pressure of the cutting blade is provided through rotational control via the depression of a button on a handle thereby removing the need to "freehand" the desemetorhexis.

2 Claims, 5 Drawing Sheets

(58) Field of Classification Search
CPC ............. A61F 9/013; A61F 9/0133; A61F 2009/00861; A61F 2009/00872; A61B 17/32; A61B 17/32002; A61B 2017/320032
See application file for complete search history.

(56) References Cited

FOREIGN PATENT DOCUMENTS

| | | |
|---|---|---|
| RU | 2647480 C1 | 3/2018 |
| WO | WO2009050511 A1 | 4/2009 |
| WO | WO-2016068163 A1 * | 5/2016 ............. A61F 9/007 |

* cited by examiner

DESCEMETORHEXIS CREATION DEVICE

CROSS-REFERENCE TO RELATED APPLICATIONS

This application claims priority from U.S. Provisional Patent Application 63/161,293 filed Mar. 15, 2021 and U.S. Provisional Patent Application 63/161,316 filed Mar. 15, 2021, which are both incorporated herein by reference.

STATEMENT OF GOVERNMENT SPONSORED SUPPORT

This invention was made with Government Support under contracts EY026877, EY028176 and RX003179 awarded by the National Institutes of Health. The Government has certain rights in the invention.

FIELD OF THE INVENTION

This invention relates to handheld surgical ophthalmic devices and methods for the creation of a descemetorhexis.

BACKGROUND OF THE INVENTION

Corneal transplantation over the last 15 years has increasingly shifted towards removal of specific diseased layers as opposed to complete removal (i.e. penetrating or full-thickness keratoplasty). In many cases, this has led to improved final visual acuity, faster recovery times, and decreased incidence of graft rejection. Conditions for which removal of a specific diseased corneal layer is indicated include Fuchs' endothelial dystrophy and Pseudophakic bullous keratopathy.

Descemetorhexis is an important step in surgical procedures aimed at the replacement and/or removal of Descemet's membrane, often just prior to transplantation of a donor cornea. Procedures that currently include descemetorhexis as a surgical step are DMEK (Descemet's membrane endothelial keratoplasty), DSEK (Descemet Stripping Endothelial Keratoplasty), and DWEK (Descemetorhexis Without Endothelial Keratoplasty)/DSO (Descemet's Stripping Only). Normally, a descemetorhexis is performed by using a reverse Sinskey hook to create a circular incision into Descemet's membrane, peeling the membrane off the posterior cornea, and then removing it from the eye using surgical forceps.

Several complications may arise from an imperfectly created descemetorhexis. Decentration of the descemetorhexis, irregular/non-circular shape, damage to adjacent endothelium, stromal scarring, and even corneal perforation are all potential complications. Suboptimal or incomplete removal of host descemet's membrane can lead to detachment/dislocation at the graft edge requiring re-bubbling or re-grafting. These complications result from the fact that current methodology is relatively imprecise and requires a "freehand" technique that is dependent on surgeon skill. There are few alternative techniques that exist for descemetorhexis creation. Femtosecond laser-assisted descemetorhexis has been studied, but is cost-prohibitive to perform widely. Additionally, not all surgical centers have a femtosecond laser needed for this, making this method limited in terms of potential for wide-spread adoption.

The present invention addresses the need for new technology to perform a reproducible, precise, centered, and circular descemetorhexis.

SUMMARY OF THE INVENTION

The present invention provides a handheld surgical ophthalmic device for the creation of a descemetorhexis. The device distinguishes a proximal drive shaft and a distal drive shaft coupled to the proximal drive shaft at one end of the proximal drive shaft. The proximal drive shaft, when actuated, rotates the distal drive shaft. A gearing mechanism is distinguished at a distal end of the distal drive shaft, which converts the rotation of the distal drive shaft to a circular motion defined in a plane perpendicular to the rotational axis of the gearing mechanism. A first arm is connected to the gearing mechanism such that it is capable of rotating the circular motion in the plane perpendicular to the rotational axis of the gearing mechanism. The first arm at its distal end has a cutting protrusion protruding more or less perpendicular to the rotational axis of the gearing mechanism. A second arm is fixed, therewith not-moveably connected, at the distal end of the distal drive shaft. The first arm is longer than the second arm, and the second arm at its distal end has a stabilization protrusion protruding more or less perpendicular to the rotational axis of the gearing mechanism and in more or less the same direction as the cutting protrusion. The second arm is positioned above the first arm relative to the gearing mechanism, and the stabilization protrusion is at a higher position than the cutting protrusion relative to the gearing mechanism.

The present invention further provides a method of creating a circular descemetorhexis. One would have or use the handheld surgical ophthalmic device as described herein. The first arm and the second arm are inserted into the anterior chamber of an eye through a corneal incision. The cutting protrusion and the stabilization protrusion are then docked on the posterior cornea. Subsequently, one would then initiate the handheld surgical ophthalmic device to perform the circular motion of the first arm and therewith the cutting protrusion whereby the cutting protrusion creates the circular descemetorhexis.

Embodiments of the present invention provide for precise concentric, symmetric, and repeatable circular scoring (cutting) of Descemet's membrane. The precision of the cut is provided by the stabilizing point (172) on the stabilizing arm (170) as well the anchoring insertion point at the limbus. Stabilization through the insertion point and the stabilizing arm provides a two-point fixation thereby establishing a cutting plane. The cutting plane allows for precise depth of cut whereas the rotating blade's consistent radius allows for circularity of the cut. The stabilization arm fixates on tissue, and is then removed when the procedure is completed. Depression of a button is directly linked to the rotation. Consequently, consistent torque and contact pressure of the cutting blade is provided through rotational control via the depression of a button on the handle of the device thereby removing the need to "free hand" the desemetorhexis. Embodiments of the invention provide stabilization, centration, precise depth of cut and consistent circular cuts, reduces abnormalities in cut shape, tags, adjacent tissue damage, and increases the chances of donor tissue engraftment.

DETAILED DESCRIPTION

The present invention provides a device and a method of using the device capable of creating a circular descemetorhexis at a predictable depth, which is technically easy for a surgeon to use and avoids damaging adjacent corneal structures. By delivering a consistent descemetorhexis, there is the important opportunity to improve surgical outcomes for corneal transplant procedures.

Figure 1:
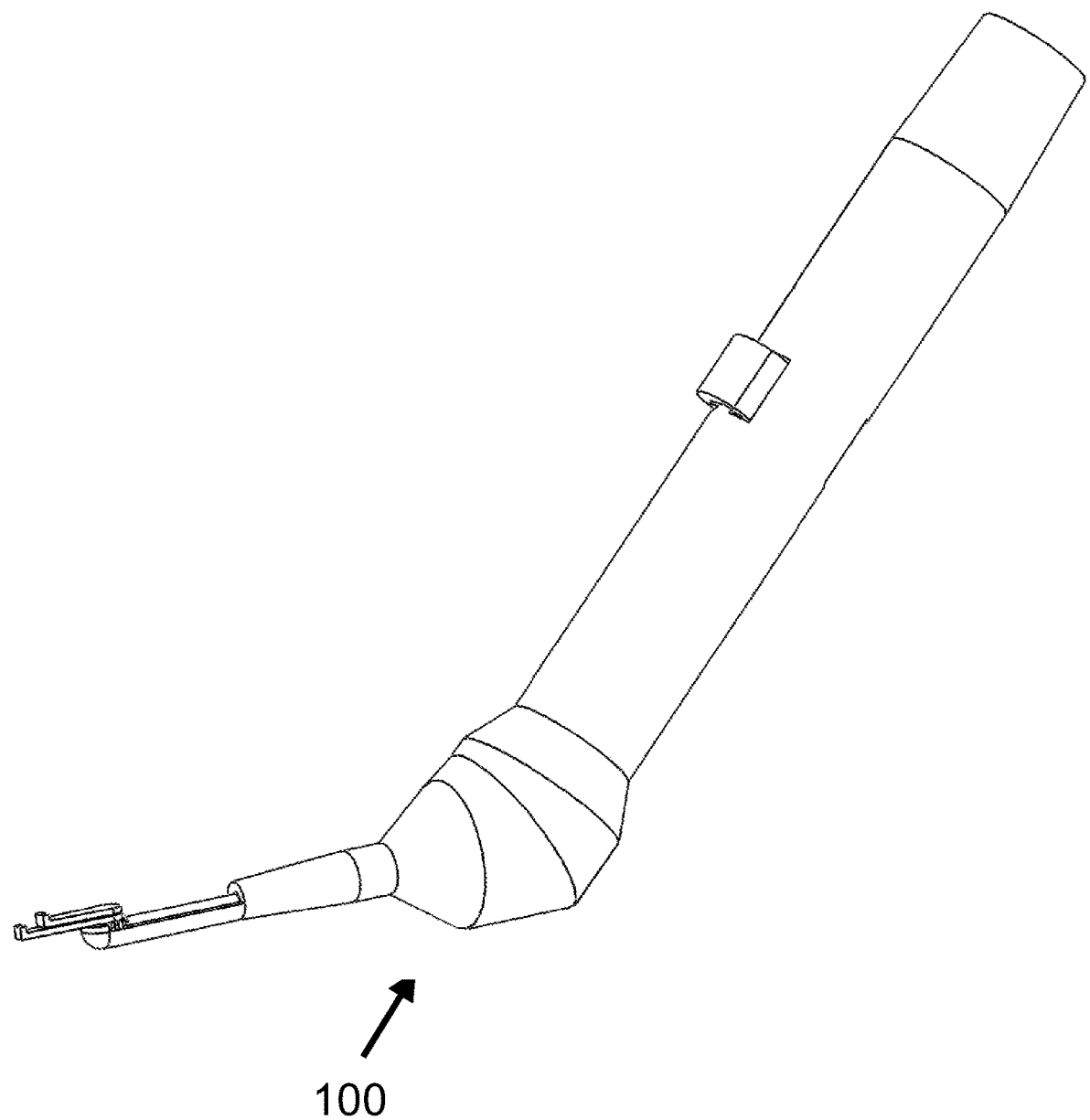
FIGS. 1-2 shows according to an exemplary embodiment of the invention the descemetorhexis creation surgical device.
Figure 2:
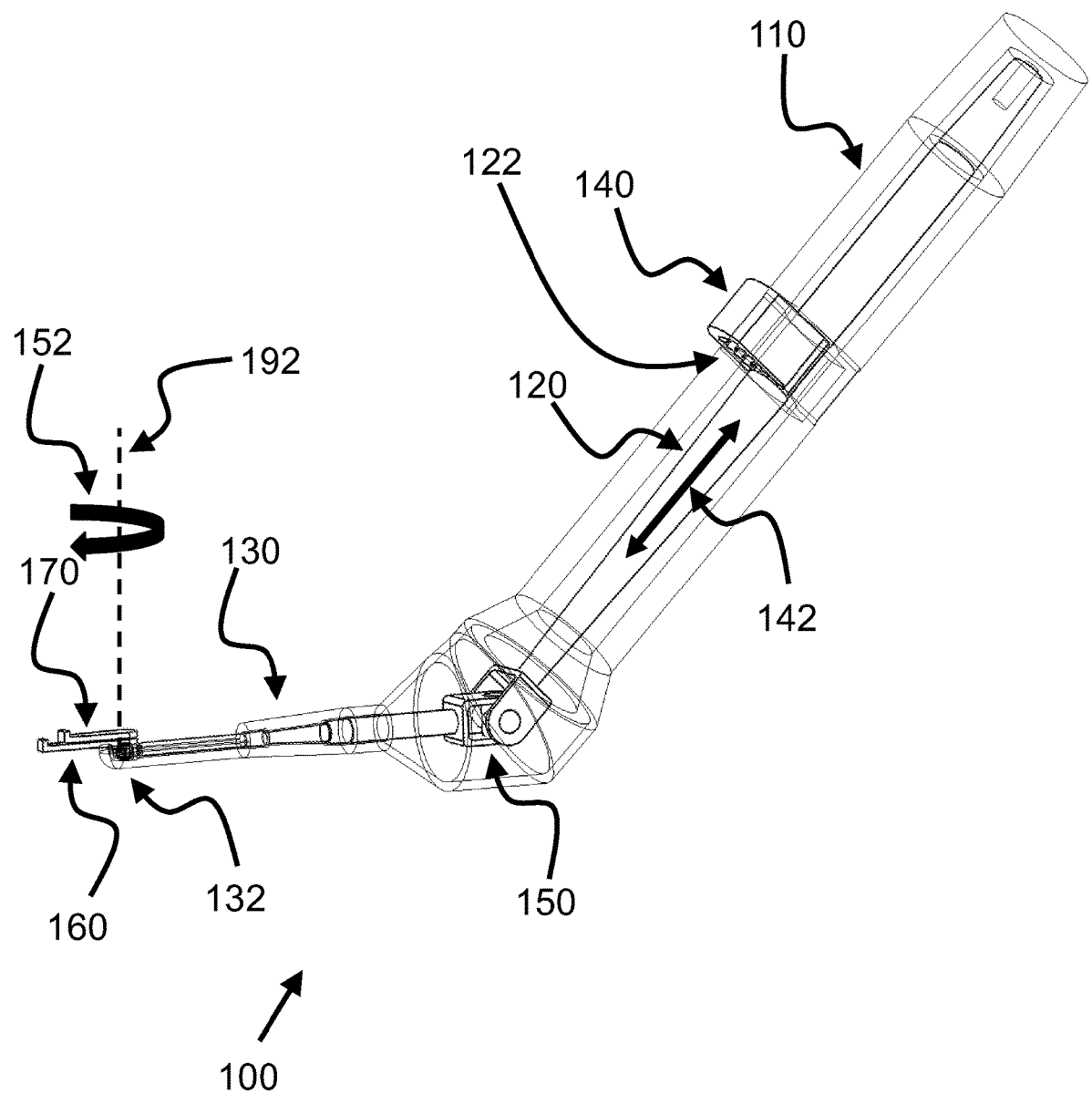
Figure 3:
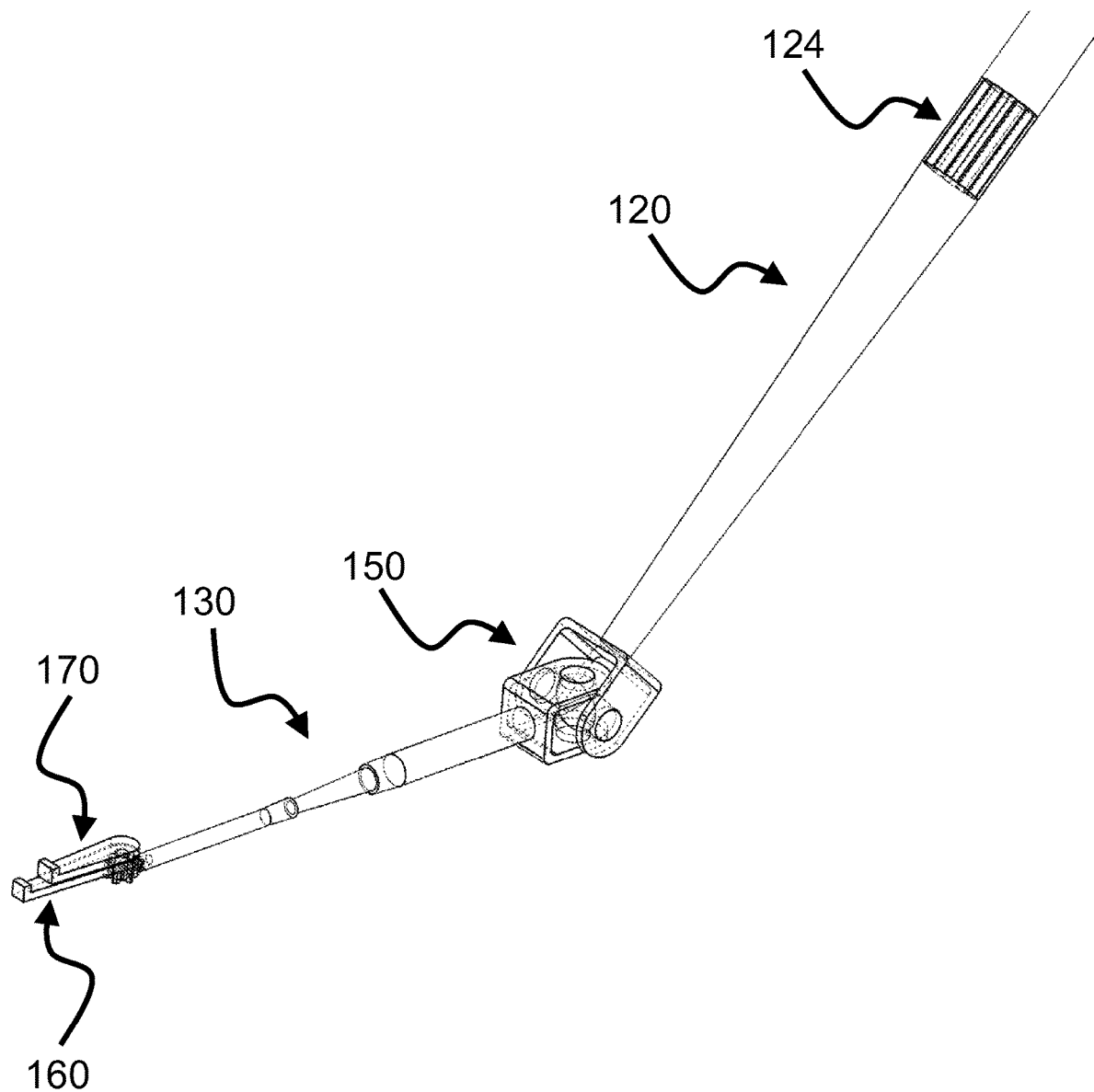
FIG. 3 shows according to an exemplary embodiment of the invention the proximal 120 and distal 130 drive shafts.

The present invention is a sterile surgical device used for descemetorhexis creation. It is a handheld instrument 100 distinguishing an outer casing 110 which covers a larger, proximal drive shaft 120 and a smaller, distal drive shaft mechanism 130 (FIGS. 1-3).

Figure 4:
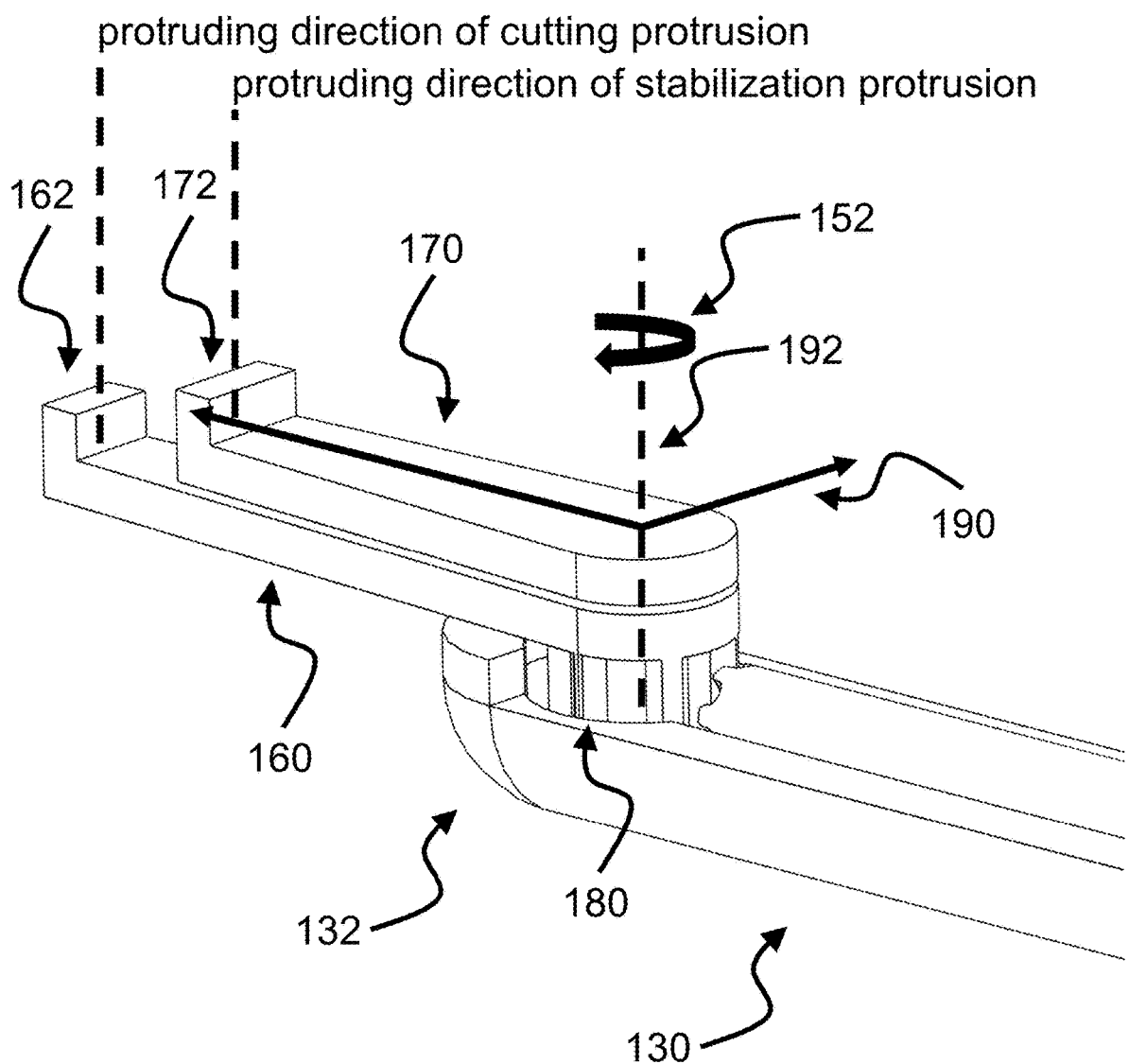
FIG. 4 shows according to an exemplary embodiment of the invention the cutting 160 and stabilization 170 elements of the device.

The proximal driveshaft 120 is actuated by a button 140 located on the handle/outer casing 110. As the proximal drive shaft 120 rotates, it turns the distal drive shaft 130 located at the end of the device. Both shafts are connected to each other by a U-shaped joint 150, which allows for the linear motion 142 originating from the handle button 140 to be transferred to the end 132 of the distal drive shaft producing circular motion 152 around the axis 192 and in the plane 190 as described in FIG. 4. Both drive shafts are housed within a silicone casing.

The mechanism of action of rotation is initiated by a mechanical button 140 through mechanical force provided either by the fingers of the user (either index of thumb) or via an electromechanical motor. The electromechanical motor can be powered by an electrical source, by internal battery, as well as external electrical power source. The mechanical button 140 has a set of linear gears 122 which engages with circular gear 124 of proximal drive shaft 120 forming a gear train (transmission) transferring linear motion into rotational motion. The universal joint 150 changes the plane of rotation. Button 140 operates on a linear plane, and the user applies mechanical force via finger or electromechanical motor the button into the handle. The linear gear of the button forms a gear train (transmission) with the circular gear of the proximal shaft thereby transferring the linear motion into rotational motion. As the mechanical force of the button is reduced (finger lifts off the button) internal springs within the button-handle mechanism returns (pushes out) the button to its original undepressed state, which allows for the cutting blade to rotate counterclockwise to its original state. This mechanism of action provides the user with precise, consistent, independent rotational control of the cutting element. In another embodiment, pressing of the button initiates a transfer of linear to rotational motion that is ultimately transferred to the cutting element via an universal joint, and finally a differential gear which transfers the plane of rotational motion by 90°. In another embodiment, the cutting blade does not rotate back to its original position after releasing the button, and pressing the button again produces additional circular motion of the cutting blade. The blade can be configured to rotate either clockwise or counter-clockwise.

There are two arms (160, 170) located at the distal tip/end 132 of the device (FIGS. 1-4):

1. A cutting protrusion element 162 protruding from cutting (first) arm 160, and
2. A stabilization protrusion element 172 protruding from stabilization (second) arm 170, and protruding in the same direction as cutting protrusion element 162.

Cutting element 162 through cutting arm 160 is attached to a gearing mechanism 180, which enables it to engage with the distal drive shaft 130 and perform rotational motion 152 in the horizontal plane 190 (identified by the two arrows/axes forming the horizontal plane 190; defined e.g. with reference to cutting element 160 and/or defined in a plane perpendicular to the rotational axis 192 of the gearing mechanism 180). Notably, rotation 152 is shown in one direction for illustration purposes only but, as a skilled artisan would readily appreciate, either or both directions are possible. Cutting element 162, when inserted into an anterior chamber 410 (FIG. 5) of an eye and appropriately engaged to the posterior cornea 422 of cornea 420 creates a circular descemetorhexis 430. Stabilization element 172 is designed to rest stationary against the posterior cornea, within the created descemetorhexis. In other words, as can be depicted from FIG. 4, stabilization arm 170 does not move with respect to the distal drive shaft 130, while the cutting arm 160 rotates to create the circular descemetorhexis 430.

Characteristics and Tissue Contact

Figure 5:
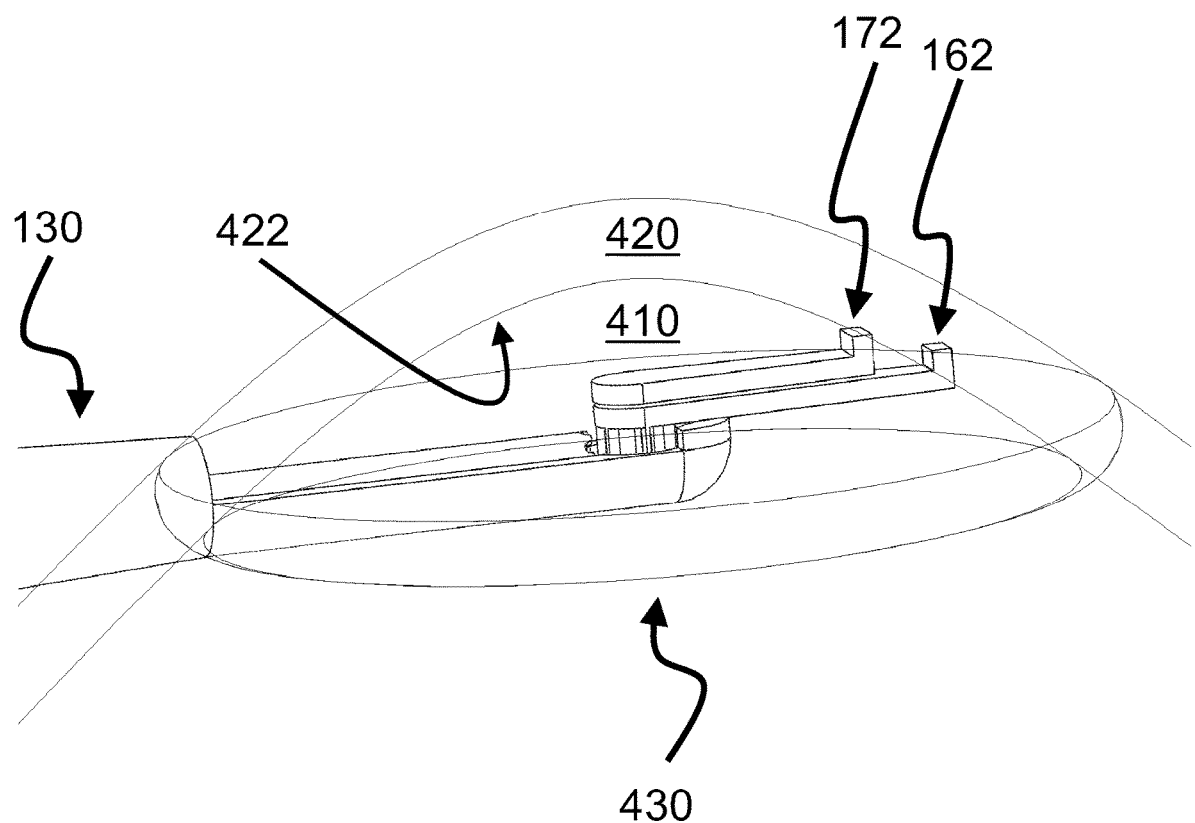
FIG. 5 shows according to an exemplary embodiment of the invention the device within the anterior chamber 410.

The device is inserted into the anterior chamber, where it will be used to create a descemetorhexis (FIG. 5).

1) The Limbus. The device is inserted through a standard sized clear corneal incision measuring approximately 2.4 millimeters in size, just anterior to the limbus. The distal aspect of the device will lie in contact with the cornea 420 at this point.
2) The Cornea Endothelium. Both the stabilization 172 and cutting 162 elements are designed to rest along the posterior cornea 422 on the endothelium. Exemplary dimensions are as follows for an 8.00 mm diameter circular cut for a typical corneal curvature. Corresponding different dimensions can be used for to produce different diameter circular cuts (either larger or smaller). Cutting element 162 is 2.77 mm longer in length than stabilization element 172. The cutting element is 8.00 mm from peripheral edge of blade to axis of rotation. Stabilization element is 2.75 mm from peripheral edge of contact point to the axis of rotation. Protrusion of the cutting element from the most proximal casing is approximately 2.77 mm. The total height from the static element to the peripheral casing is approximately 2.68 mm. The stabilization element is approximately 0.25 mm higher than the cutting element. Diameter of circular axis of rotation is approximately 2.0 mm (column diameter that rotates). Larger or smaller circular cuts can be created by varying the dimensions of the aforementioned elements. During descemetorhexis creation, any endothelium contacting the stabilization element will be removed.

Surgical Instrumentation/Implantation

The device is to be used with a standard set of cornea surgical instrumentation. Preferably, the device is intended for single use only. In another embodiment, the device is sterilizable and re-usable. The surgical technique for its use is as follows (FIG. 5):

An inferior peripheral iridotomy is created or is pre-existing from a prior procedure.

A temporal clear corneal incision made using a standard sized keratome (~2.4 mm), as well as one superior and one inferior paracentesis. The device may also be larger in diameter, which would require larger corneal incisions (e.g. 2.8 mm or larger).

Cohesive viscoelastic is then injected into the anterior chamber 410. (Alternatively, air can be instilled instead, or continuous irrigation of sterile saline solution from the device itself).

The device is then carefully inserted into the anterior chamber 410 through the corneal incision, and the cutting 162 and stabilization 172 elements are docked on the posterior cornea.

Button 140 on the handle is depressed, and cutting element 162 is engaged and rotated 360 degrees for circular 430 descemetorhexis creation. Multiple rotations can be implemented. (Alternatively, multiple cutting elements can reduce degrees of rotation).

The device is then carefully removed from the anterior chamber 410.

The Descemet's membrane is then peeled away from the posterior stroma and is then carefully removed from the anterior chamber 410 with forceps.

If viscoelastic is used, it is then removed from the anterior chamber.

For endothelial transplantation, graft donor tissue is inserted into the eye and adhered to the posterior stroma via established endothelial keratoplasty procedures (e.g. transplantation of endothelial cells on either a lamellar (posterior cornea) graft or descemet's membrane with intraocular air or gas bubble placement underneath the graft). Alternatively, cultured endothelial cells can be placed using various procedures with or without a carrier or intervening attachment or adhesive layer. In some embodiments, no endothelial cells transplanted, to allow for central migration and proliferation of host peripheral endothelial cells with or without pharmacologic treatment to encourage this cell re-growth.

Surgical closure, medications, and patching are completed per standard ophthalmic surgical procedure.

The device has the ability to create a well-centered 360-degree circular score in descemet's membrane at the appropriate depth, minimizing the incidence of irregular tags, decentration, or posterior stromal damage.

In another embodiment, the device has an internal port within a handle to allow saline solution to be irrigated while the device is within the anterior chamber to maintain internal ocular pressure.

Magnetic Descemetorhexis Creation Device

In another embodiment, the invention is a magnetic handheld surgical ophthalmic device and method for the creation of a descemetorhexis, which are described in U.S. Provisional Patent Application 63/161,316 filed Mar. 15, 2021, which are both incorporated herein by reference for all that is teaches. In brief, an extraocular magnet is used anterior to the corneal to control the movement, position, and contact pressure of an intraocular descemet's membrane cutting element, and then the scored descemet's membrane is peeled and removed from the eye as described above, followed by optional endothelial cell transplantation. In another embodiment, an extraocular magnet is used only to stabilize and centrate the intraocular descemetorhexis creation device, but the magnet does not serve to produce motion in the intraocular device. In this case, a portion of the descemetorhexis creation device is ferro-magnetic, so that it can dock to the undersurface of the cornea through magnetic force applied by the extraocular magnet.

What is claimed is:

1. A handheld surgical ophthalmic device for the creation of a descemetorhexis, comprising:
   (a) a proximal drive shaft;
   (b) a distal drive shaft coupled to the proximal drive shaft at one end of the proximal drive shaft, wherein the proximal drive shaft, when actuated, rotates the distal drive shaft;
   (c) a gearing mechanism at a distal end of the distal drive shaft, wherein the gearing mechanism translates the rotation of the distal drive shaft to a circular motion having a rotational axis;
   (d) a first arm laterally extending away perpendicular from the rotational axis and connected to the gearing mechanism such that it is therewith capable of rotating in the circular motion in a plane more or less perpendicular to the rotational axis, wherein the first arm at a distal end of the first arm has a cutting protrusion protruding in a protruding direction more or less parallel to the rotational axis of the gearing mechanism; and
   (e) a second arm laterally extending away from the rotational axis and wherein the second arm is fixed, therewith not-moveably connected, at the distal end of the distal drive shaft, wherein the first arm is longer than the second arm, wherein the second arm is superior to the first arm wherein superior is defined relative to the plane more or less perpendicular to the rotational axis, wherein the second arm at a distal end of the second arm has a stabilization protrusion protruding more or less parallel to the rotational axis of the gearing mechanism and in more or less the same direction as the protruding direction.

2. A method of creating a circular descemetorhexis, comprising:
   (a) having a handheld surgical ophthalmic device, wherein the handheld surgical ophthalmic device comprises:
      (i) a proximal drive shaft;
      (ii) a distal drive shaft coupled to the proximal drive shaft at one end of the proximal drive shaft, wherein the proximal drive shaft, when actuated, rotates the distal drive shaft;
      (iii) a gearing mechanism at a distal end of the distal drive shaft, wherein the gearing mechanism translates the rotation of the distal drive shaft to a circular motion having a rotational axis;
      (iv) a first arm laterally extending away from the rotational axis and connected to the gearing mechanism such that it is therewith capable of rotating in the circular motion in a plane more or less perpendicular to the rotational axis, wherein the first arm at a distal end of the first arm has a cutting protrusion protruding in a protruding direction more or less parallel to the rotational axis of the gearing mechanism; and
      (v) a second arm laterally extending away perpendicular from the rotational axis and wherein the second arm is fixed, therewith not-moveably connected, at the distal end of the distal drive shaft, wherein the first arm is longer than the second arm, wherein the second arm is superior to the first arm wherein superior is defined relative to the plane more or less perpendicular to the rotational axis, wherein the second arm at a distal end of the second arm has a stabilization protrusion protruding more or less parallel to the rotational axis of the gearing mechanism and in more or less the same direction as the protruding direction;
   (b) inserting the first arm and the second arm into an anterior chamber through a corneal incision;

(c) docking the cutting protrusion and the stabilization protrusion on a posterior cornea; and
(d) initiating the handheld surgical ophthalmic device to perform the circular motion of the first arm and therewith the cutting protrusion whereby the cutting protrusion creates the circular descemetorhexis.

* * * * *